United States Patent [19]
Beal et al.

[11] Patent Number: 5,482,183
[45] Date of Patent: Jan. 9, 1996

[54] HEATER AND DISPENSER FOR VIALS

[76] Inventors: Jeff R. Beal, 3901 Diadem; Mike T. Kalinowski, Sr., 5103 Redding Dr., both of San Antonio, Tex. 78219

[21] Appl. No.: 315,967

[22] Filed: Sep. 30, 1994

[51] Int. Cl.⁶ .................................................. G07F 11/72
[52] U.S. Cl. ..................... 221/150 A; 221/256; 221/271; 221/274; 221/281
[58] Field of Search ................................ 221/150 A, 155, 221/199, 256, 271, 274, 281

[56] References Cited

U.S. PATENT DOCUMENTS

| | | | |
|---|---|---|---|
| 924,407 | 6/1909 | Whitcomb | 221/155 |
| 979,318 | 12/1910 | Marriott | 221/271 X |
| 1,678,355 | 7/1928 | Roberts | 221/271 X |
| 1,699,608 | 1/1929 | Cooke | 221/155 |
| 1,861,834 | 6/1932 | Binggeli | 221/274 X |
| 2,218,041 | 10/1940 | Hutaff, Jr. | 221/271 |
| 3,162,322 | 12/1964 | Gilbertson | 221/135 |
| 4,117,956 | 10/1978 | von Schuckmann | 221/288 |
| 4,473,180 | 9/1984 | Lowrance et al. | 227/48 |
| 4,700,048 | 10/1987 | Levy | 221/150 A X |
| 4,790,324 | 12/1988 | O'Hara et al. | 128/664 |
| 4,932,789 | 6/1990 | Egawa et al. | 374/126 |
| 5,100,018 | 3/1992 | Rosati et al. | 221/6 |
| 5,310,084 | 5/1994 | Pittman | 221/199 X |

*Primary Examiner*—William E. Terrell
*Assistant Examiner*—Dean A. Reichard
*Attorney, Agent, or Firm*—Gunn, Lee & Miller

[57] ABSTRACT

A device for heating and manually dispensing small vials or carpules. The device includes a generally rectangular housing having a top wall with a lid. The lid provides access to the interior of the housing. The interior of the housing includes a vial feed chamber and a sliding dispensing member. The interior of the housing is heated with a small incandescent light bulb. The dispensing member has a notch near the leading edge for loading vials when in a retracted position and dispensing vials when in an extended position, the extended position reaching beyond the housing of the dispenser.

9 Claims, 3 Drawing Sheets

5,482,183

HEATER AND DISPENSER FOR VIALS

FIELD OF THE INVENTION

A dispenser for heating and dispensing vials of medicine, more specifically, a vial or carpule dispenser having a housing within which is contained vials for dispensing and a small incandescent bulb for heating the vials.

BACKGROUND OF THE INVENTION

A vial dispenser, especially a dispenser for dispensing small vials of medicine, is a convenient accessory for doctors' and dentists' offices. A vial dispenser which maintains the vials at a temperature above room temperature, as by heating, is sometimes helpful, especially for medicine such as novocaine or other local anesthetics. It is more comfortable to the patient if the medication with which they are injected is at a temperature greater than room temperature, typically about normal body temperature.

Article dispensers, some of which maintain articles in a heated state are disclosed in the prior art. It is understood that the terms vial, ampule and carpules are used interchangeably and refer to small, typically cylindrical containers holding a liquid—typically a single dose of medicine.

For example, U.S. Pat. No. 3,162,322 (Gilbertson 1964) discloses a dispenser for cartridges such as carpules which are gravity fed single file through a channel to a spring bias sliding door. The Gilbertson device does not provide for heating the cartridges.

U.S. Pat. No. 4,117,956 (Von Schuchann 1978) discloses a receptacle for dispensing tablets which gravity feeds tablets into a slot from which the tablet is ejected by actuating a sliding member.

U.S. Pat. No. 4,790,324 (O'Hara et al. 1988) discloses a receptacle for holding disposable probes, the probes held in a fixed position within a tray. A heating element in a hand-held probe unit is disclosed. A digital read-out indicates the temperature of the probe.

U.S. Pat. No. 4,932,789 (Egawa et al. 1990) discloses a temperature sensitive probe with a disposable head.

U.S. Pat. No. 5,100,018 (Rosati 1992) discloses a probe cover dispenser which includes a slide and indentation for receiving a disposable probe.

None of the prior art vial dispensers, however, provide for a device capable of maintaining vials in a heated chamber above room temperature typically between about 80° and 100°, while dispensing them from a lever actuated dispensing member. More specifically, none of the prior art devices provide for a simple, mechanically actuated dispensing drawer combined with a gravity feed carpule chamber which is maintained at above room temperature through the use of a small incandescent lamp.

Applicant's combination of a simple, mechanically actuated dispensing drawer along with a low wattage incandescent bulb provides for a simple, inexpensive, easy to manufacture and use, ampule dispensing device for use in doctors' or dentists' offices.

SUMMARY OF THE INVENTION

The objects of applicant's present invention are provided for in a heated ampule dispenser having a housing comprised of a rectangular wall structure having a top wall with a pivoting lid, the housing enclosing an interior compartment heated by a small incandescent bulb and having a feed compartment for loading a sliding dispensing drawer, actuated by a handle, the drawer in a normally dispensing position allowing access to the ampule by the user.

DETAILED DESCRIPTION OF THE PREFERRED EMBODIMENT

Figure 1:
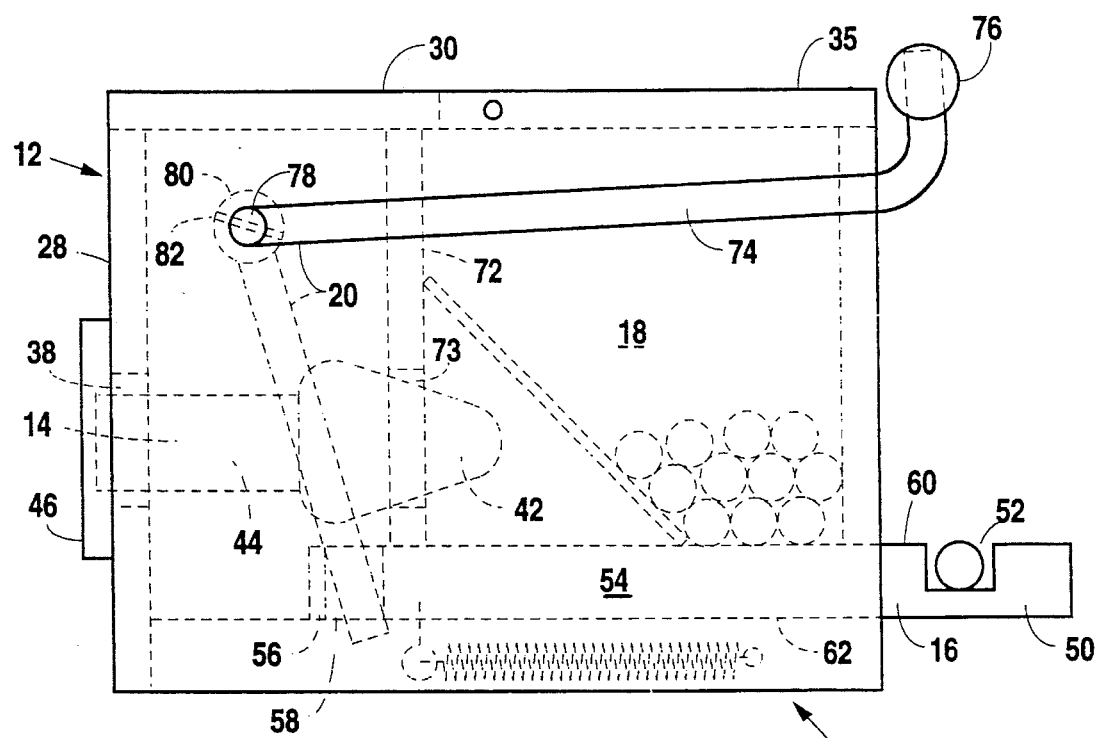
FIGS. 1 and 2 are side elevation views of the left side (as seen from the front) of applicant's vial dispenser in a normal or extended position with the vial dispensed (FIG. 1) and in an engaged or retracted position with the handle depressed (FIG. 2).
Figure 2:
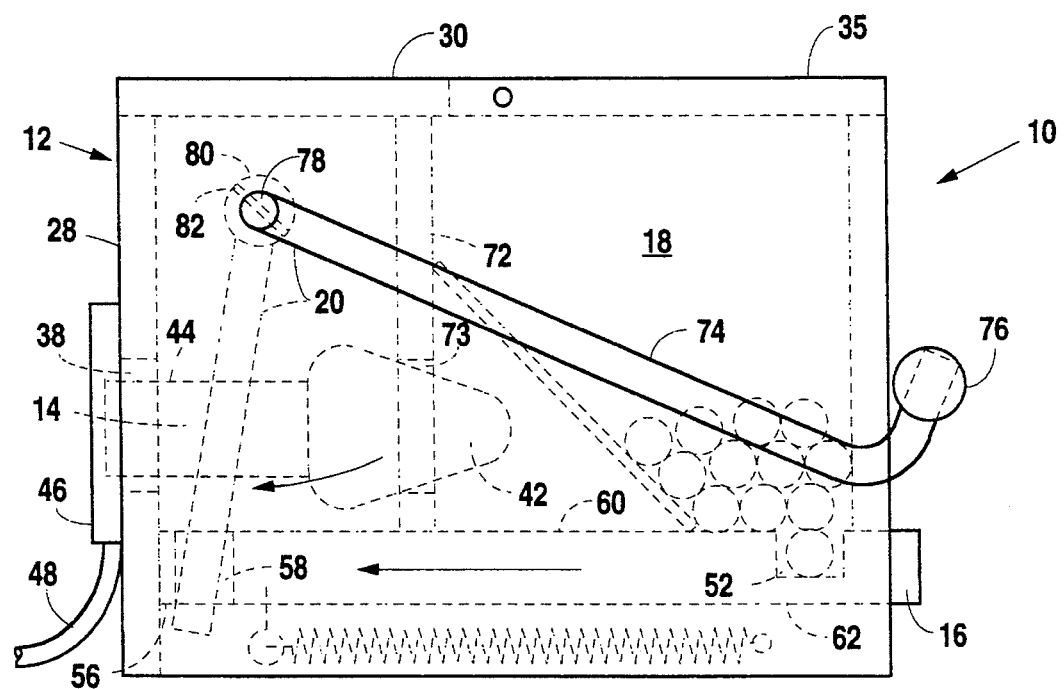
Figure 3:
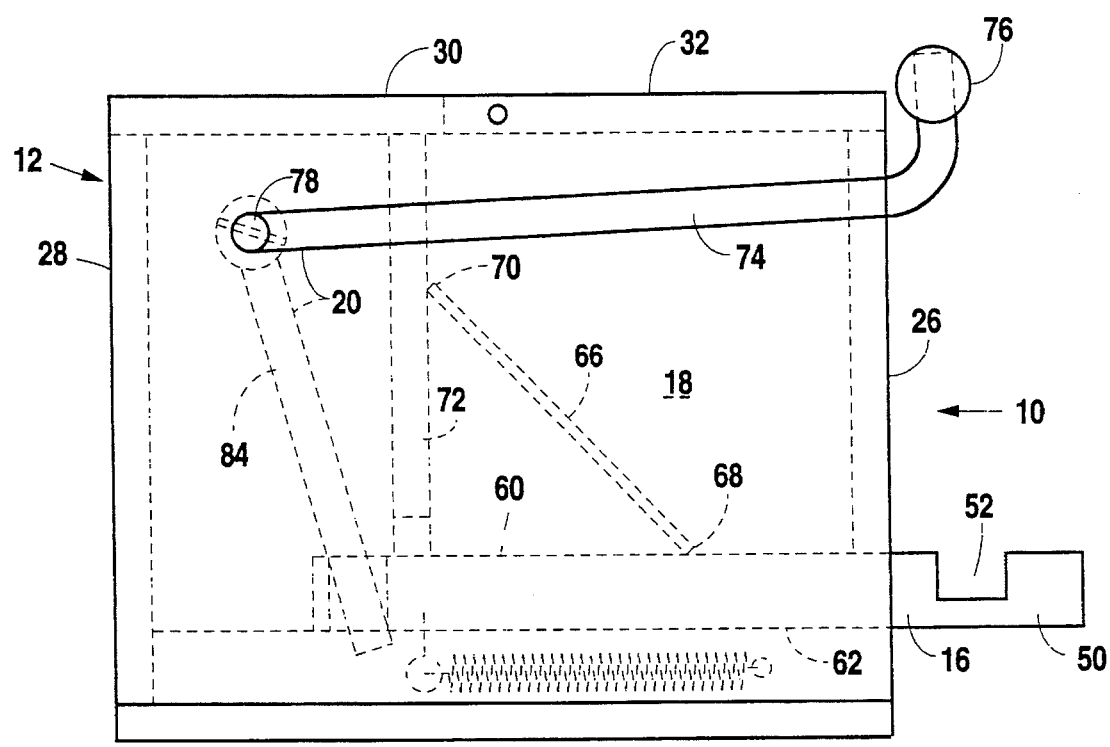
FIG. 3 is a left side elevation view of the ampule dispenser of applicant's present invention with the incandescent bulb removed therefrom.

FIGS. 1–6 show various views of vial dispenser (10) of applicant's present invention. Vial dispenser (10) is seen to be comprised of a generally rectangular housing (12), the housing defining the exterior of the vial dispenser and substantially enclosing an interior thereto. FIGS. 1 and 2 illustrate the manner in which the interior of housing (12) is heated, specifically the use of an incandescent light bulb (14). Carpules or vials, such as those illustrated in FIGS. 1 and 2, are stacked within the interior of housing (12) to engage a dispensing member (16) which is seen in FIG. 1 in a normal or extended position, providing access to the dispensed ampule and in FIG. 2, in an engaged or retracted position in which the ampule or vial is loaded onto the dispensing member. More details of these features will be provided as set forth below.

Enclosed in housing (12) is vial or ampule feed chamber (18) which is designed to load or gravity feed the carpules onto dispensing member (16) when the dispensing member is in the retracted position. It is seen in FIGS. 1 and 2 how actuator means (20) engages dispensing member (16) to move the dispensing member between a normal or extended position and an engaged or retracted position.

Turning now to the details of housing (12), it is seen in FIGS. 1–6 that housing (12) is comprised of a left side wall (22) (as seen from the front of the vial dispenser), a right side wall (24), a front wall (26), a rear wall (28) and a top wall (30). Alternatively, a bottom wall (31) may be provided (see FIGS. 3 and 4). The walls are typically made of flat stock, plastic approximately ¼ inch thick but up to ½ inch thick and are glued together to form a generally rectangular shape and to substantially enclose the interior of the vial dispenser.

Figure 4:
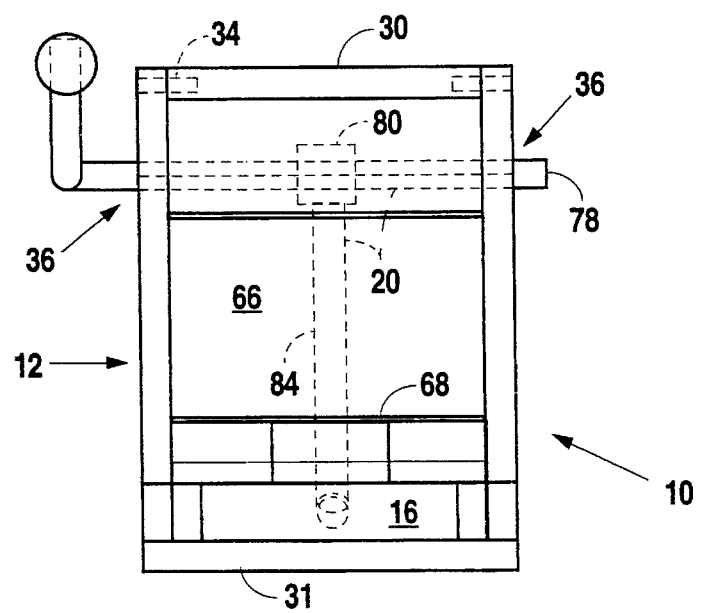
FIG. 4 is a front elevation view of the ampule or vial dispenser of applicant's present invention.

The various walls of housing (12) are modified or altered in a number of ways. First, it is seen that top wall (30) contains a pivoting lid (32) which engages the top of left side wall (22) and right side wall (24) at pins (34). Typically, the lid and/or front wall maybe clear plastic for visually determining the need for refilling without opening the lid. Leading edge (35) of pivoting lid (32) may be grasped to raise the lid and provide access to vial feed chamber (18) to insert new vials or carpules thereinto. Both left and right side walls are seen to have holes (36) therethrough with which to engage actuating means (20) in a manner as more specifically set forth below. Likewise, rear wall (28) has a hole (38)

therein, allowing for the insertion of incandescent bulb (14) therethrough. Last, it is seen that front wall (26) has an elongated slot (40) at the bottom, which slot is designed to allow the receipt of dispensing member (16) therethrough as illustrated in FIGS. 1, 2 and 4.

Turning now to the details of incandescent light bulb (14), it is seen that the light bulb is comprised of an incandescent lamp (42), typically 4 watts, but in the range of 2 to 6 watts, which is threadably received into a socket (44), which is in turn adapted to a plastic mounting plate (46) which engages rear wall (28), typically by screws (not shown). An insulated electrical cord (48) with a switch (not shown) completes the details of incandescent bulb (14) and is provided with a plug for insertion into a 120 volt AC electrical outlet. The bulbs and socket used with applicant's dispenser are similar to those used with residential night lights.

Reference to FIGS. 1–6 illustrate the features of dispensing member (16). More specifically, it can be seen that dispensing member (16) is generally tabular in shape and has a leading edge (50) with a receiving notch (52), dimensioned for receipt of carpules or vials therein. It is to be appreciated with reference to FIGS. 1 and 2 that receiving slot (52) is dimensioned such that, when a vial rests in the receiving slot, there is sufficient clearance in the slot (40) allow the dispensing member to slide out.

Figure 5:
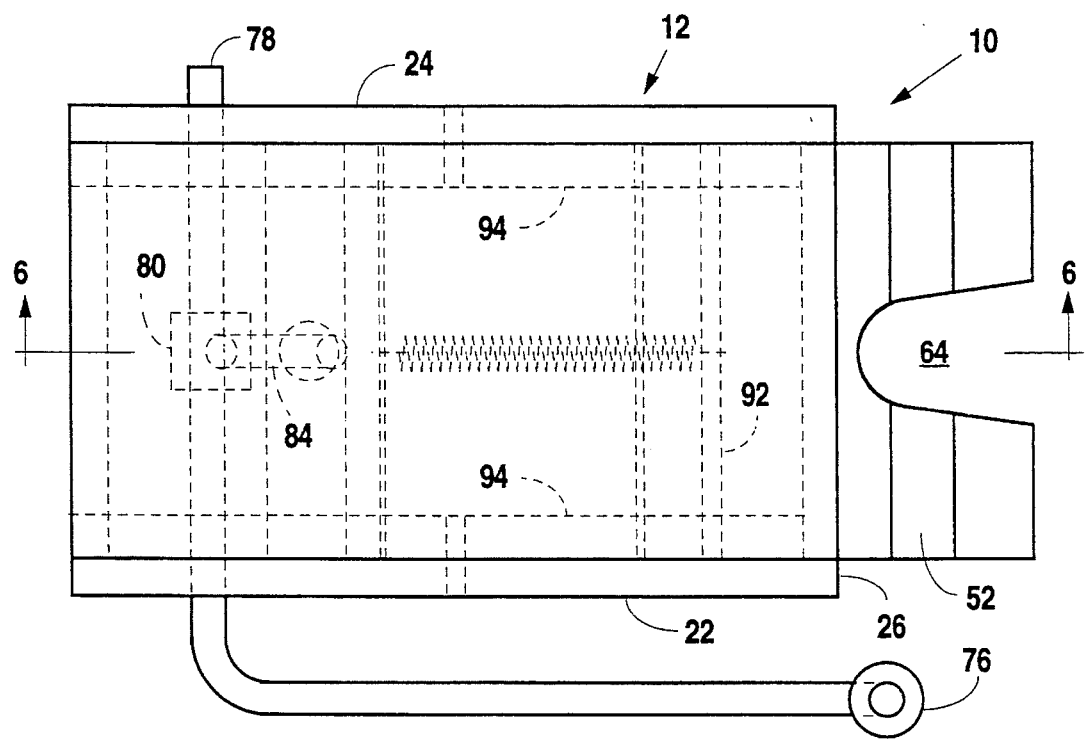
FIG. 5 is a top view of the vial dispenser of applicant's present invention.

Dispensing member (16) is seen to have a generally tabular body (54) with a trailing edge (56) on the opposite end of leading edge (50). Adjacent trailing edge (56) and midway between the distal edges of the dispensing member is located a hole (58) for engagement with actuating means (20) as more specifically set forth below. The dispensing member also has top surface (60) and bottom surface (62). It is seen in FIG. 5 how leading edge (50) has an indent (64) therein. The use of indent (64) allows the consumer to place a finger underneath the ampule to grasp it between its thumb and forefingers as it lays in receiving notch (52).

Turning now to the features of vial feed chamber (18), it is seen that a slant wall (66) provides a means of gravity feeding the carpules to receiving notch (52) in top surface (60) of dispensing member (16). Typical carpules will contain 1.8 ml. of novocaine. The typical vial chamber will hold 40 carpules when full. It is seen with reference to FIG. 2 that the carpules are directed towards the receiving notch by the slant wall. More specifically, slant wall (66) has a bottom edge (68) and a top edge (70). It is positioned at an angle against partition (72). That is, the top edge of slant wall (66) rests against partition (72) and is typically glued. Bottom edge (68) stands away from the partition so as to feed the carpules to the dispensing member.

Partition (72) provides hole (73) for partial insertion of lamp (42) into vial chamber (18) and helps provide heating of the vials through conduction across slant wall (66). It is noted that only about one-third to one-half of the forward portion of the lamp projects into chamber (18). This prevents the vials from getting too warm. Further, partition (72) acts as a bulkhead to provide structural integrity to housing (12). Last, partition (72) acts to absorb heat from lamp (42) and disperse the same throughout vial feed chamber (18). Partition (72) has, near the bottom edge thereof, slot (73a) to allow dispensing member (16) to slide back and forth as it is actuated through actuator means (20).

Figure 6:
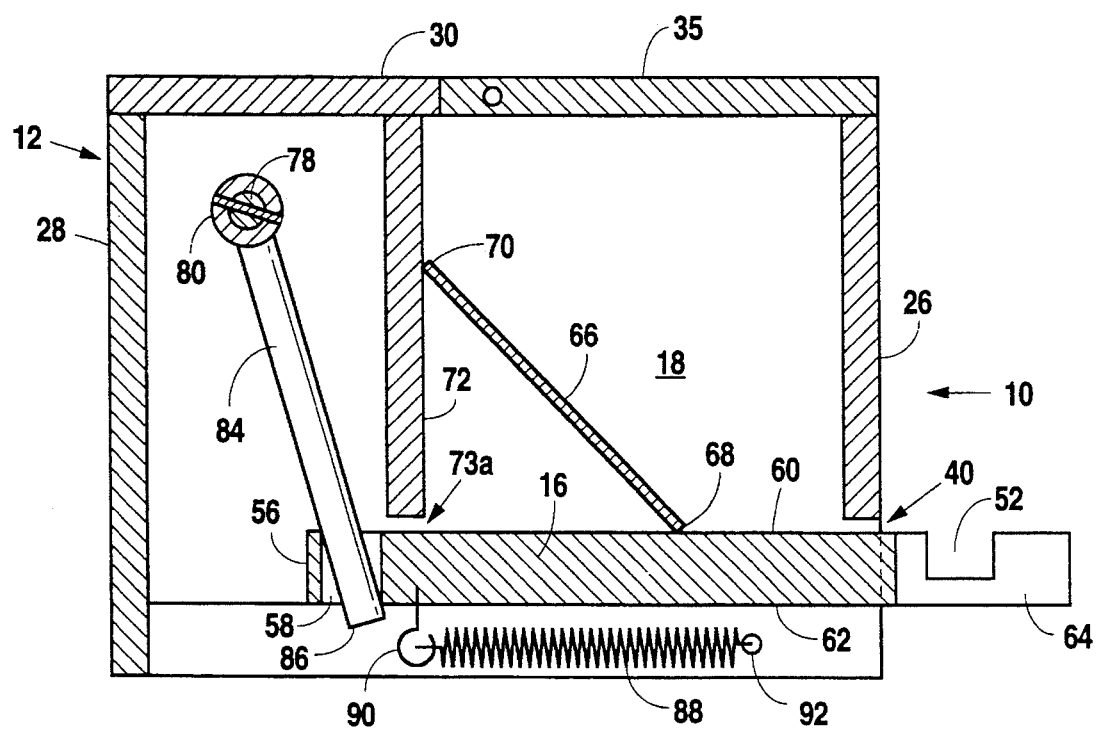
FIG. 6 is a cut-away side elevation view through "Section A—A" of applicant's present invention.

Actuator means (20) is seen to have an elongated, cylindrical handle (74) with a knob (76) at the distal end thereof. The handle is integral with an axle (78) which articulates on left side wall (22) and right side wall (24) at holes (36). Handle (74) and axle (78) are typically made of ¼ inch round stock steel. It is seen in FIGS. 5 and 6 how axle (78) is provided with a collar (80) typically located centrally, allowing the axle between the two side walls. Collar (80) is engaged with axle (78) through pin (82) such that movement of the axle (through actuating the handle) causes rotation of the axle/collar unit. Further, it seen with reference to FIGS. 5 and 6 that collar (80) is integral with depending lever (84). Lever (84) has removed end (86) which engages hole (58) adjacent the trailing edge of dispensing member (16) as set forth in FIG. 6. Spring or bias means (88) is engaged at one end through fastener (90) to bottom surface (62) of dispensing member (16). At a second end, spring (88) is attached to rod (92) which is permanently fastened to a pair of support rails (94) located laterally just inside the lower edges of the left and right side walls as indicated in FIG. 5. Rod (92) supports and locates one end of spring (88). Spring (88) will urge dispensing member (16) towards a normally dispensed or extended position as set forth in FIGS. 1, 3, 5 and 6. When pressure (see FIG. 2) is exerted on the knob of handle (74), rotation of axle (78) urges removed end (86) of lever (84) in a clockwise direction as illustrated in FIG. 2. This action slides dispensing member (16) to a retracted position as illustrated in FIG. 2. In this position, an ampule or vial will be downloaded into receiving notch (52). Subsequent release of knob (76) allows dispensing member (16) to return to its normally extended or dispensing position as illustrated in FIG. 1.

In use with a 4 watt bulb, inserted into hole (73) as illustrated in FIGS. 1 and 2 and energized through a 120 volt AC outlet, applicant's invention will maintain glass carpules of 1.8 ml. novocaine at between 80° and 100° F. in a room at a temperature of about 70° F. With a full vial chamber, it takes about sixty minutes to warm up. Typically, the light is left on all working week but turned off on non-working weekends.

It is to be appreciated that applicant's invention provides for a small, efficiently constructed and easy to use vial dispenser that provides a heated vial feed chamber in which a small, low wattage incandescent bulb provides sufficient heat to maintain the vials at a warm temperature.

The general dimensions set forth below, when used with materials set forth above, along with the wattage indicated in the power of the lamp, will provide an appropriate temperature in the vials such that upon use, will be neither too warm nor too cool for the patient.

|  | LENGTH | WIDTH | THICKNESS |
| --- | --- | --- | --- |
| Front Wall | 3–5" | 2½"–3½" | ⅛–⅜" |
| Right Side Wall | 4–6" | 3¼"–4¾" | ⅛–⅜" |
| Left Side Wall | 4–6" | 3¼"–4¾" | ⅛–⅜" |
| Rear Wall | 3–5" | 2½"–3½" | ⅛–⅜" |
| Top Wall | 4–6" | 2½"–3½" | ⅛–⅜" |
| Partition | 3–5" | 2½"–3½" | ⅛–⅜" |
| Dispensing Member | 3–5" | 2¼"–3¼" | ¼–¾" |

While applicant's vial dispenser is designed to dispense carpules, the same could be provided, with the dimensions changed accordingly, without a heating element and designed with a small, appropriate sized, receiving notch and therefore, capable of dispensing smaller articles such as, for example, toothpicks.

Terms such as "left," "right," "up" "down," "bottom," "top," "front," "back," "in," "out," and like are applicable to the embodiments shown and described in conjunction with the drawings. These terms are merely for purposes of description and do not necessarily apply to the position or manner in which the invention may be constructed for use.

Although the invention has been described in connection with the preferred embodiment, it is not intended to limit the invention's particular form set forth, but on the contrary, it is intended to cover such alternatives, modifications, and equivalencies that may be included in the spirit and scope of the invention as defined by the appended claims.

What is claimed is:

1. A device for heating and manually dispensing small vials, the device comprising:

a housing, said housing having walls, the walls including two side walls, a top wall a front wall, and a rear wall, the walls defining an interior, the top wall including an access member for providing access to the interior of said housing;

an incandescent light bulb, said incandescent light bulb being located substantially within said housing for heating the interior thereof;

a dispensing member, said dispensing member having a receiving notch thereon, said dispensing member slidingly engaging said housing and movable between an extended position for dispensing a vial and a retracted position for reloading the receiving notch of said dispensing member with a new vial;

walls defining a feed chamber, wherein said walls defining the feed chamber include a partition, the partition including an access port for receipt of said incandescent light bulb therein, said feed chamber capable of containing a multiplicity of small vials, said walls including at least one slanted wall, the slanted wall for urging the vials towards the receiving notch of said dispensing member, and for allowing the vials to fall into the receiving notch of said dispensing member; and actuating means, said actuating means including a handle extending beyond said housing, said actuating means engaging said dispensing member to move said dispensing member between the extended and the retracted positions when the handle is manually engaged.

2. The device of claim 1, wherein said incandescent light bulb is mounted to the rear wall of said housing such that it extends partially but not completely through the access port of said partition into the feed chamber.

3. The device of claim 2, wherein said incandescent light bulb is rated between and including 2 to 6 watts and includes an insulated electric cord for engaging a 120 volt AC power source.

4. The device of claim 2, wherein said incandescent light bulb is of sufficient power to maintain the vials at a temperature of between 80° and 100° F. when ambient temperature is about 70° F.

5. The device of claim 1, wherein said dispensing member includes a leading edge dimensioned to include an indent for grasping and for removing the vial from the receiving notch.

6. The device of claim 1 further including bias means for urging said dispensing member towards the extended position.

7. The device of claim 1, wherein the width of the feed chamber is about 2¾ inches.

8. The device of claim 1, wherein the walls of said housing and said walls of the feed chamber are tabular, made of plastic, between ⅛ to ⅜ inch thick, with the exterior of said housing being generally rectangular in shape and having a length between 4 and 6 inches, a width of between 2¼ and 3¾ inches and a height of between 3¾ and 4¾ inches.

9. A device for heating and manually dispensing small vials, the device comprising:

a housing, said housing having walls, the walls including two side walls, a front wall, a top wall, and a rear wall, the walls of said housing being tabular, made of plastic between ⅛ and ½ inch thick, with the exterior of said housing being generally rectangular in shape and having a length between 4 and 6 inches, a width between 2¼ and 3¾ inches and height between 3¾ and 4¾ inches, the top wall of said housing including a pivoting lid for providing access to an interior of said housing, wherein either of the front wall or the lid of the top wall are made of transparent plastic;

an incandescent light bulb, said incandescent light bulb engaging and supported by the rear wall of said housing, said incandescent light bulb having a power rating between 2 and 6 watts and including an insulated electric cord for engaging a 120 volt AC power source, wherein said incandescent light bulb is of sufficient power to maintain the vials at a temperature between 80° F. and 100° F. when the ambient temperature is about 70° F.;

a dispensing member, said dispensing member having a receiving notch thereon, said dispensing member slidingly engaging said housing and movable between an extended position for dispensing a vial and a retracted position for reloading the receiving notch of said dispensing member with a new vial, wherein said dispensing member includes a leading edge dimensioned to include an indent portion for grasping and removing the vial from the receiving notch when said dispensing member is in the extended position;

walls defining a feed chamber, said feed chamber capable of containing a multiplicity of small vials wherein the width of the feed chamber is about 2¾ inches, said walls including at least one slanted wall, the slanted wall for urging the vials towards the receiving notch of said dispensing member, the slanted wall terminating above the receiving notch, thus allowing the vials to fall into the receiving notch under the impetus of gravity, the walls of the feed chamber including a partition, the partition having an access port for the receipt of said incandescent light bulb partially but not completely therethrough;

actuating means, said actuating means including a handle extended beyond said housing, said actuating means engaging said dispensing member to move said dispensing member between the extended and the retracted position when the handle is manually engaged; and bias means for urging said dispensing member towards the extended position.

* * * * *